US00PP17466P2

(12) United States Plant Patent
Schlueter

(10) Patent No.: US PP17,466 P2
(45) Date of Patent: Mar. 6, 2007

(54) ***HIBISCUS ROSA-SINENSIS* PLANT NAMED 'HOLLYWOOD'**

(50) Latin Name: *Hibiscus rosa-sinensis*
Varietal Denomination: Hollywood

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 5 days.

(21) Appl. No.: 11/213,646

(22) Filed: Aug. 19, 2005

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
(74) *Attorney, Agent, or Firm*—Chrisite, Parker & Hale, LLP

(57) ABSTRACT

A new and distinct cultivar of *Hibiscus* plant named 'Hollywood', characterized by a large ruffled flower with a red center, transitioning to orange with yellow edges, and metallic silver veining evident in the red and orange areas. 'Hollywood' is a free flowering plant with an upright, compact habit, and glossy, dark green foliage.

4 Drawing Sheets

Botanical classification: *Hibiscus rosa-sinensis* L.
Varietal denomination: The new plant has the varietal denomination 'Hollywood'.

BACKGROUND OF THE INVENTION

The present invention relates to a new and distinct cultivar of *Hibiscus,* botanically known as *Hibiscus rosa-sinensis* and hereinafter referred to by the cultivar name 'Hollywood'.

The genus *Hibiscus* comprises about 250 species of herbs, shrubs and trees in warm temperate and tropical regions; with leaves usually simple, mostly palmately veined, lobed or parted; flowers are mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves grow to 6-inches in length, and are ovate, usually serrate, mostly glossy green. Flowers are solitary in upper leaf axils.

The new *Hibiscus* is a product of a planned breeding program conducted by the Inventor in Webster, Tex. The objective of the program was to create new *Hibiscus* selections with improved bloom quality, color and floriferousness. A further objective was to produce plants that can be commercially produced on their own root systems, with improved plant habit, with regard to vigor and postproduction longevity.

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy dark green foliage;
3. Vigorous growth habit;

4. Large ruffled flower with a red center, transitioning to orange with yellow edges. Metallic silvery veining is evident in the red to orange zones; and
5. Free flowering.

SUMMARY OF THE INVENTION

The cultivar 'Hollywood' has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'Hollywood'. These characteristics in combination distinguish 'Hollywood' as a new and distinct cultivar:

1. Upright, compact symmetrical plant habit that is suitable for container production
2. Healthy dark green foliage.
3. Vigorous growth habit.
4. Large ruffled flower with a red center, transitioning to orange with yellow edges. Metallic silvery veining is evident in the red to orange zones.
5. Free flowering.

Asexual reproduction of the new variety by stem cuttings, performed in Webster, Tex. and Houston, Tex., have confirmed that the distinctive characteristics of the new variety are stable and transmitted to succeeding generations, and the new variety reproduces true to type.

COMPARISON WITH PARENTS AND OTHER CULTIVARS

'Hollywood' is distinguished from its female parent 'Georgia's Pearl' (not patented) by its plant habit: 'Georgia's Pearl' is taller, with less branching. 'Hollywood' is distinguished from its male parent 'Jason Blue' (not patented) in the flower color: 'Jason Blue' has an orange yellow flower with a silvery blue eye, while 'Hollywood' has a flower with a red center, transitioning to orange with yellow edges.

The closest commercial cultivar to 'Hollywood' known by the Inventor is 'Georgia's Pearl'. However, in side-by-side comparisons conducted in Webster, Tex., plants of 'Hollywood' differ from plants of 'Georgia's Pearl' in the following characteristics:

1. Flowers of the new *Hibiscus* have a different color pattern than flowers of the cultivar 'Georgia's Pearl';
2. Plants of the new *Hibiscus* are easier to clone via rooting than plants of the cultivar Georgia's Pearl; and
3. Plants of the new *Hibiscus* are more compact, with a better branching habit, than the cultivar 'Georgia's Pearl'.

'Hollywood' also has a sibling, namely the *Hibiscus rosa-sinensis* 'Enlightenment' (U.S. Plant patent application Ser. No. 11/207,517). Although these plants are closely related, they both have distinctive flower coloration. Specifically, the two flowers differ in the following ways:

1. 'Hollywood' has a red center, 'Enlightenment' does not;
2. The dominant colors on 'Hollywood's' flower are red, orange and yellow, and for 'Enlightenment' it is pink, orange and yellow; and
3. 'Hollywood' has silver veining transitioning from the red center into the orange while 'Enlightenment' does not.

BRIEF DESCRIPTION OF THE DRAWINGS

The accompanying illustrations show a specimen of the new cultivar in a photographic illustration as true to color as is reasonably possible to make in an illustration of this character. Color values in the illustrations may differ slightly from the color values cited in the detailed botanical description, which accurately describes the actual colors of the new *Hibiscus*.

DETAILED DESCRIPTION OF THE INVENTION

Figure 1:
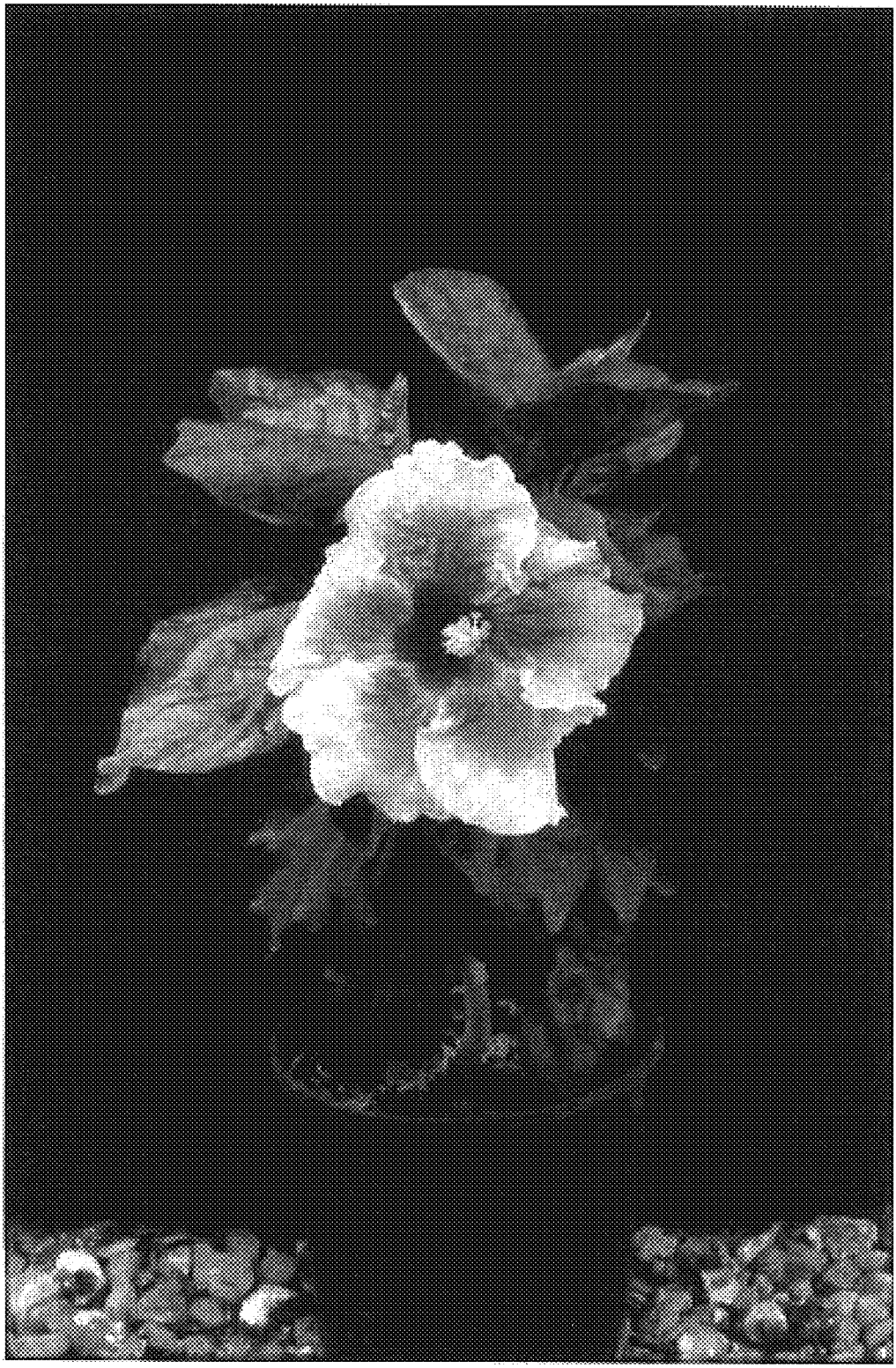
FIG. 1 illustrates a side perspective view of a typical plant of 'Hollywood'.
Figure 2:
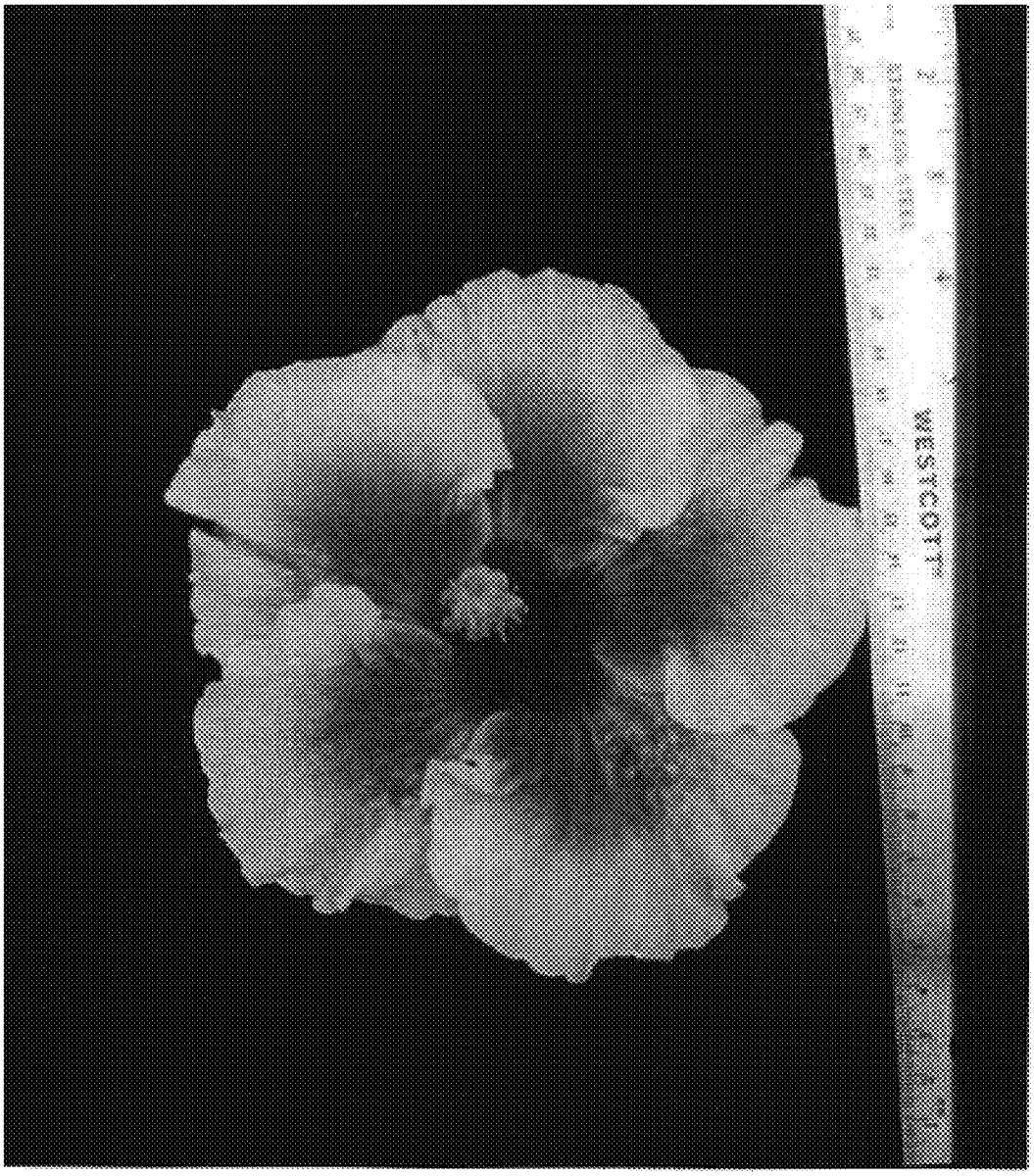
FIG. 2 illustrates the scale of a typical flower of 'Hollywood'.
Figure 3:
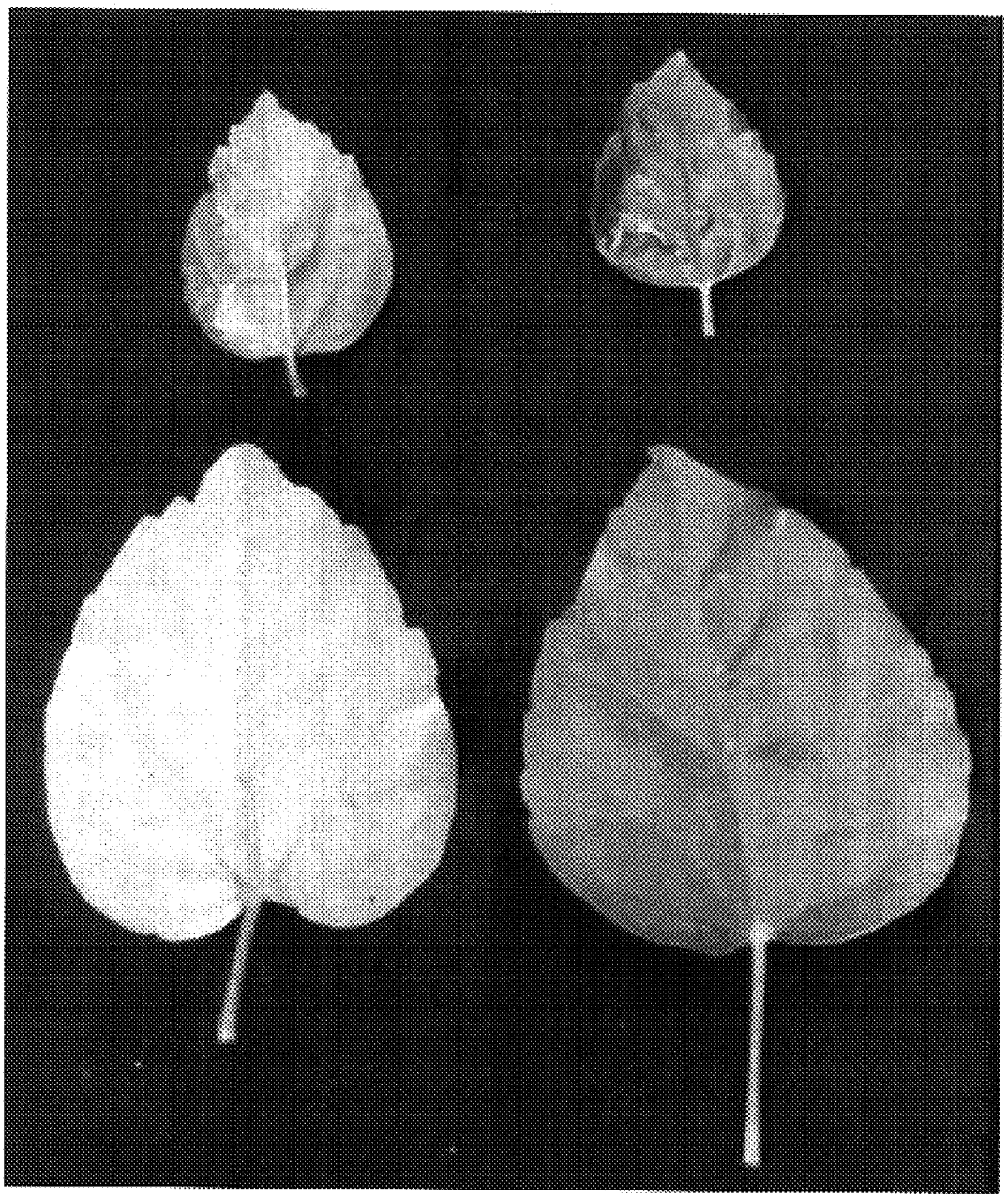
FIG. 3 illustrates the typical young to mature foliage of 'Hollywood'; the abaxial and adaxial surfaces are shown at each stage.
Figure 4:
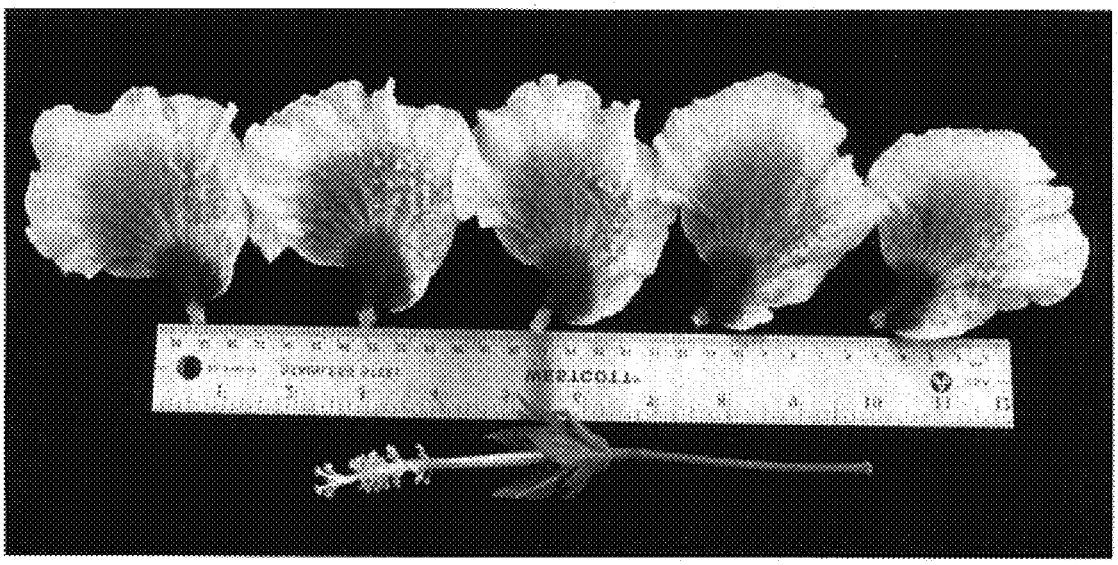
FIG. 4 illustrates a dissected flower of 'Hollywood', including shape and size of petals and characteristics of the reproductive structures.

'Hollywood' has not been observed under all possible environmental, cultural and light conditions. The following observations and descriptions are of plants grown in Fulshear, Tex., in April 2005, under polypropylene shade-cloth providing a 30 percent light reduction, and under conditions which closely approximate commercial production. Plants described were approximately one year old.

In this description, color references are to The Royal Horticultural Society Colour Chart (4th Edition) and terminology used in the color descriptions herein refers to plate numbers in this color chart. Phenotypic expression may vary with light intensity, cultural and environmental conditions.

Classification:

*Botanical.*—*Hibiscus rosa-sinensis* 'Hollywood'.

*Parentage.*—Female or Seed Parent: *Hibiscus rosa-sinensis* 'Georgia's Pearl'. Male or Pollen Parent: *Hibiscus rosa-sinensis* 'Jason Blue'.

*Propagation.*—By cuttings.

*Time to initiate rooting.*—Approximately 14 to 21 days at 21–24° C.

*Time to develop roots.*—Approximately 42 to 56 days at 21–24° C.

*Root description.*—Fine to medium; fibrous; freely branching.

Plant:

*Size.*—Height: Approximately 45–50 cm in a #2 pot (from soil level to top of flowers). Diameter/Spread: Approximately 40–45 cm in a #2 pot.

*Form and growth habit.*—Perennial, evergreen shrub; mostly upright and somewhat spreading.

*Branching.*—Freely branching, about 4 to 8 lateral branches develop after pinching. Lateral Branches: Approximately 20 cm long and 4 mm in diameter. Color: Young — 146B. Mature — 195B. Internode Length: Approximately 3 cm.

Leaf:

*Shape.*—Cordate. Apex: Obtuse. Base: Cordate.

*Leaf size.*—Approximately 11 cm long and 9.5 cm wide.

*Arrangement.*—Alternate, single, symmetrical.

*Margin.*—Crenate.

*Aspect.*—Undulate.

*Texture.*—Glabrous.

*Coloration.*—Young Foliage Upper side: Near Yellow-Green Group 147A. Under side: Near Yellow-Green Group 147B. Mature Foliage Upper side: Near Yellow-Green Group 147A. Under side: Near Yellow-Green Group 147B.

*Petioles.*—Size: Approximately 4 cm in length; approximately 3 mm in diameter. Coloration: Near Yellow-Green Group 147A. Texture: Smooth.

Inflorescence:

*Bloom period.*—Typically year-round under subtropical and tropical conditions.

*Flower arrangement.*—Arranged singly at terminal leaf axils; free flowering with 3 to 4 flower buds and/or open flowers per terminal apex; flowers face upright and slightly outward.

*Flower appearance.*—Ruffled flower with a red center, transitioning to orange with yellow edges; metallic silvery veining is evident in the red to orange zones; flowers are open for about two days before closing, flowers persistent.

*Flower diameter.*—Approximately 16 cm.

*Flower depth.*—When placed on a horizontal plane, the flower extends 6 cm above the surface, with the ruffled petals extending 1.5 cm above the plane.

*Buds* (*just prior to showing color*).—Rate of Opening: Approximately 1 or 2 days, depending on temperature. Shape: Elliptic. Length: Approximately 3.5 cm. Diameter: Approximately 2 cm. Color: Near Yellow-Green Group 146B.

*Fragrance.*—None noted.

*Petals.*—Number/Arrangement: Corolla consists of 5 overlapping petals. Shape: Spatulate with rounded apex. Size: Approximately 8 cm long and 8 cm wide. Margin: Entire, but ruffled. Texture: Smooth. Base Descriptor: Oblique. Color Upper Surface: The eye or throat is near 53A and transitions outward to a mixture of N25B&C ending in 6B on the edges; the metallic vein color is near N155A. Lower Surface: Majority of the flower surface is near 6C, fading to near 6D at the base of the petal.

*Sepals.*—Number/Arrangement: 5 sepals fused into a star-shaped calyx. Shape: Linear with acuminate apices. Margin: Entire. Color: Near Yellow-Green Group 146A.

*Peduncles.*—Length: Approximately 4 cm. Diameter: Approximately 3 mm. Angle: Upright to about 45 degrees. Strength: Strong, flexible. Color: Near Yellow-Green Group 146B.

Reproductive organs:

*Androecium.*—Stamens: Numerous; approximately 50. Stamen Length: Approximately 5 mm. Filament Color: Near White Group 155B. Anther Size: Approximately 1 mm long×1 mm wide. Pollen Amount: Abundant. Pollen Color: Near Yellow Group 7B.

*Gynoecium.*—Pistil Length: Approximately 7 cm. Stigma Appearance: Five, rounded. Stigma Diameter: Approximately 2 mm. Stigma Color: Near Orange-Red Group 32A. Style Color: Base near 53A, transitioning to between 52C and 52D, with the top third near 155B. Seed Production: Has not been observed.

Pests/diseases: Resistance to known *Hibiscus* diseases had not been observed on plants grown under conditions approximating commercial practices.

What is claimed is:

1. A new *Hibiscus rosa-sinensis* plant named 'Hollywood', substantially as shown and described.

* * * * *